United States Patent [19]
O'Neill et al.

[11] Patent Number: 5,811,584
[45] Date of Patent: Sep. 22, 1998

[54] PREPARATION OF TETRAMETHYLETHYLENEDIAMINE

[75] Inventors: Gerald J. O'Neill, Arlington, Mass.; Albert H. Levesque, Nashua; Robert J. Bulka, Merrimack, both of N.H.

[73] Assignee: Hampshire Chemical Corp., Lexington, Mass.

[21] Appl. No.: 902,460

[22] Filed: Jul. 29, 1997

[51] Int. Cl.$^6$ .................................................. C07C 209/00
[52] U.S. Cl. .............................................................. 564/494
[58] Field of Search ............................................. 564/494

[56] References Cited

U.S. PATENT DOCUMENTS

| | | | |
|---|---|---|---|
| 3,565,957 | 2/1971 | Mirviss et al. | 260/583 |
| 4,681,948 | 7/1987 | Worley | 548/319 |
| 4,721,811 | 1/1988 | Sherwin et al. | 564/491 |
| 4,845,297 | 7/1989 | Kumoi et al. | 564/487 |
| 5,097,072 | 3/1992 | O'Neill et al. | 564/491 |

FOREIGN PATENT DOCUMENTS

| | | |
|---|---|---|
| 2 248 265 | 5/1975 | France . |
| 32 48 326 | 6/1984 | Germany . |
| 1 356 455 | 6/1974 | United Kingdom . |
| 2 067 191 | 1/1981 | United Kingdom . |

OTHER PUBLICATIONS

Journal of the American Chemical Society; Dec. 15,(1971); pp. 6831–6836.
German Ref: Beilstein. vol. 1. p. 153.
Journal of the American Chemical Society; vol. 75. pp. 1478–1480 (1953).
Journal of the American Chemical Society— vol. 76. pp. 956–959 (1954).

*Primary Examiner*—Johann Richter
*Assistant Examiner*—Joseph Murray
*Attorney, Agent, or Firm*—Nields, Lemack & Dingman

[57] ABSTRACT

Process for the production of TMEDA in high yield by reducing 2,3-dimethyl-2,3-dinitrobutane with hydrogen in the presence of a chromium promoted Raney cobalt catalyst. A solution of 2,3-dimethyl-2,3-dinitrobutane in a suitable solvent is fed to a reactor while avoiding the accumulation of 2,3-dimethyl-2,3-dinitrobutane in the reaction medium, such as by feeding it at a rate no greater than its rate of reaction with hydrogen. In a preferred embodiment, the resulting TMEDA is recovered by converting it to an amine salt by sparging carbon dioxide through the solution.

12 Claims, No Drawings

PREPARATION OF TETRAMETHYLETHYLENEDIAMINE

BACKGROUND OF THE INVENTION

A conventional method for the preparation of tetramethylethylenediamine (TMEDA) has been by reduction of 2,3-dimethyl-2,3-nitrobutane (DMDNB) with tin or zinc and hydrochloric acid. This process is cumbersome and uneconomical and generates a significant waste stream.

As described in *J. Am. Chem. Soc.* 75, 1478 (1953), 2,3-diamino-2,3-dimethylbutane was prepared by the reduction of 2,3-dinitro-2,3-dimethylbutane with zinc and concentrated hydrochloric acid, which resulted in a 40% yield. That paper also discloses that catalytic reduction with platinum or Raney nickel and hydrogen gives very poor yields of impure product. Indeed, a later paper by the same authors (*J. Am. Chem. Soc.* 76, 956 (1953)) states that attempts to prepare sufficient quantities of 2,3-diamino-2,3-dimethylbutane for the studies undertaken were not successful.

U.S. Pat. No. 4,681,948 discloses the preparation of N-chloro and N-bromo derivatives of 2-imidazolidinones having substituents at the 4- and 5-positions of the ring. The '948 patent teaches that unhalogenated tetraalkyl substituted 2-imidazolidinones may be prepared by first reducing the corresponding 2,3-dialkyl-2,3-dinitrobutane to the 2,3-dialkyl-2,3-diaminobutane by the method described by J. Bewad in the article entitled *Concerning Symmetrical Tertiary alpha Dinitroparrafin*, Ber., 39, 1231–1238 (1906). Although such a procedure has been used successfully, it is inefficient.

GB 1,356,455 discloses a process for the preparation of aliphatic, unbranched $C_6$–$C_{18}$ diamines from the corresponding aliphatic unbranched $C_6$–$C_{18}$ dinitriles, hydrogen and ammonia in the presence of a hydrogenation catalyst, by hydrogenating to form diamines at elevated temperatures and pressure, and monoamines or compounds which form monoamines under the reaction conditions, said monoamines or compounds being added to the dinitriles prior to the reaction.

GB 2,067,191 discloses a method of hydrogenating polynitriles to polyamines using a pelleted cobalt-zinc hydrogenation catalyst usually in oxide form.

It would be advantageous to develop an efficient, alternative procedure for the preparation of TMEDA in high yield.

It would further be advantageous to develop an efficient procedure for the recovery of TMEDA thus produced.

SUMMARY OF THE INVENTION

The problems of the prior art have been solved by the instant invention, which provides a process for the production of TMEDA in high yield by 1) reducing 2,3-dimethyl-2,3-dinitrobutane with hydrogen in the presence of a chromium promoted Raney cobalt catalyst; and 2) feeding a solution of 2,3-dimethyl-2,3-dinitrobutane to a reactor while avoiding the accumulation of 2,3-dimethyl-2,3-dinitrobutane, such as by carrying out the addition thereof at a rate no greater than its rate of reaction with hydrogen. Minimizing the accumulation of 2,3-dimethyl-2,3-dinitrobutane in the reaction medium prolongs catalyst life. In a preferred embodiment, the resulting TMEDA is recovered by converting it to an amine salt by sparging carbon dioxide through the solution.

DETAILED DESCRIPTION OF THE INVENTION

The present invention is directed to a process for producing tetramethylethylene diamine in high yield by reducing 2,3-dimethyl-2,3-dinitrobutane with hydrogen by feeding a solution of 2,3,-dimethyl-2,3-dinitrobutane to a reactor such that little or no 2,3-dimethyl-2,3-dinitrobutane accumulates during the reaction. This is preferably accomplished by feeding the 2,3-dimethyl-2,3-dinitrobutane at a rate no greater than its rate of reaction with hydrogen. The reaction is conducted in the presence of a chromium promoted Raney cobalt catalyst.

The catalyst preferably is a finely-divided chromium Raney® cobalt which has a particle size of from 20 to 50 microns mean diameter. The Raney® cobalt catalyst should contain from about 0.5 to about 3.5 weight percent of chromium. The catalyst should be charged into the reactor in an amount of from about 5% to about 20%, preferably 10% to 15% and most preferably about 15% by weight based on the weight of the 2,3-dimethyl-2,3-dinitrobutane to be reacted. The preferred catalyst for use in the present reaction is a chromium-promoted Raney® cobalt catalyst commercially available under the designation Raney® cobalt 2724 from the Davison Chemical Division of W. R. Grace & Co.-Conn., and is supplied with an average 30 micron particle size. The catalyst is relatively sensitive to oxygen and thus must be handled carefully to avoid surface oxidation. Nitrogen sparging of the reactant solutions and the storage of the same under nitrogen blankets is effective to exclude oxygen from the system. The catalyst particles are washed with deionized and deaerated water and then with a deaerated inert solvent (preferably the same solvent used to prepare the feedstock solution) prior to use.

The catalyst is formed from an initial alloy which contains from about 50 to about 70 weight percent aluminum, from about 30 to about 50 weight percent cobalt, and from 0 to about 6 weight percent chromium. Chromium may also be provided by treating the surface of an already activated alloy with a salt of these materials to provide from 0.1 to about 5 percent of chromium on the Raney® cobalt surface. The most preferred catalyst is formed from alloys having from 0.5 to 5.0 weight percent chromium.

The initial alloy is contacted with an aqueous alkaline solution formed from an alkali or alkaline earth metal hydroxide, preferably sodium hydroxide. The alloy should have a particle size of from about 20 to about 50 microns mean diameter. The activation is carried out in a known manner by contacting the starting alloy with dilute, normally from about 1 to 10 weight percent, preferably from 1 to 5 weight percent, alkaline solution while maintaining a low temperature such as below about 50° C. and preferably below 40° C. Generally, it is best to activate the alloy at from about 20° to 40° C. Activation is readily monitored by the evolution of hydrogen and provides a suitable catalyst for use in the instant process when from 20 to 40 percent of the aluminum is removed. The activated Raney® cobalt catalyst is washed with water to free it from the alkaline solution and is used immediately or stored under water or other inert medium or atmosphere.

Preferred hydrogenation apparatus for use in the instant invention is a stirred autoclave, which is a pressure vessel fitted with an agitator and cooling coils for heat removal, and means for introducing the feedstock therein during the pressurized reaction. Internal or external heating coils may be used to heat the reactants, preferably to a temperature of about 80° C.

The 2,3-dimethyl-2,3-dinitrobutane starting material preferably is provided in a feedstock solution with an inert solvent. Suitable inert solvents include N,N-dimethylacetamide (DMAC), methanol, ethanol and methyl ethyl ketone (MEK). Those skilled in the art will appreciate that the amount of inert solvent used depends on the identity of the particular solvent and the desired concentration of DMDNB, with the maximum concentration being limited by the operating temperature of the hydrogenation process. Since the concentration of the dinitrobutane is only about 11% at ambient temperature, it is preferred that the temperature in MEK, for example, of the feedstock solution be raised to avoid the necessity of removing (such as through distillation) the otherwise large volumes of solvent that would be required to generate suitable product yields. Based on the solubility data set forth below, the temperature range of the feedstock should be between 0° C. and 110° C., preferably between about 20° C. to about 105° C., more preferably between about 50° C. and 105° C. The feedstock in some cases has to be pressurized to achieve higher concentrations of DMDNB at temperatures above the solvent boiling point.

| Temp. (°C.) | Solub. (Wt. %) | Temp. (°C.) | Solub. (Wt. %) |
|---|---|---|---|
| MEK | | DMAC | |
| 25 | 11 | 25 | 16 |
| 50 | 23 | 50 | 21 |
| 70 | 35 | 70 | 36 |
| ETHANOL | | METHANOL | |
| 75 | 9 | 70 | 9 |
| 90 | 20 | 90 | 26 |
| 105 | 43 | 105 | 47 |

Consistent with standard hydrogenation practice, a reactor is brought to the desired temperature and pressure (the operable pressure range for hydrogenation being from about 50 to about 1500 psig, with a pressure range of between about 75 and 150 psig being preferred), and a small amount of the finally divided catalyst is placed within the reactor vessel. The material to be hydrogenated (the substrate) may be continuously added in the form of a solution in the inert solvent, and the contents are agitated. Hydrogen is introduced at the desired pressure whereupon the reaction progresses to completion. Following completion of the hydrogenation reaction, the liquid contents of the vessel are separated from the solid catalyst. This separation can be accomplished by discharging the entire contents of the reactor vessel into a holding tank and then filtering the catalyst, or by allowing the catalyst to settle in the reactor and then removing the supernatant liquid via a dip tube in the reactor vessel.

The reaction rate can be determined by trial and error, using space velocity as an indicator, where space velocity (SV) is:

$$SV = (\text{pounds of organic feed/hour})/(\text{pounds of catalyst})$$

Since DMDNB is a catalyst poison, if a certain feed rate (space velocity) is exceeded, an accumulation of unreacted DMDNB occurs, which poisons the catalyst, reducing its activity and resulting in a product yield decrease. A space velocity range from 0.1 to 10, preferably 2 to 5, depending on temperature and pressure, can be used to ensure that a proper relationship between the feed rate of DMDNB and the amount of catalyst in the system is maintained, so that the DMDNB is fed to the system at a rate equal to or slower than its reaction rate with hydrogen. In this way, unreacted DMDNB does not accumulate and poison the catalyst.

Hydrogen uptake can be optionally measured by any suitable means, or the progress of the reaction can be followed by in-process analysis. The latter procedure is preferable since it would detect any accumulation of unreacted DMDNB.

The reaction can be run in a continuous mode in the slurry reactor such as by maintaining a continuous purge and removing solution through an internal filter arrangement at approximately the same rate at which the DMDNB/MEK solution is being added to the reactor. The reaction solution can be removed either continuously or at suitable intervals, i.e., intermittently. If the reaction is run in a continuous mode in a trickle bed reactor, a higher pressure on the order of about 2500 psig is required to maximize yields.

TMEDA sublimes readily and therefore comes over with solvent distillate. In order to recover the TMEDA from solution, it can be converted to an acid salt, preferably the diacetate, which can then be separated from the solvent.

In an especially preferred embodiment, the TMEDA is recovered by forming the amine salt, and then converting the salt to TMEDA. The amine salt (which is a mixture of carbamate and carbonate salts) can be formed by sparging $CO_2$ through a solution containing crude TMEDA at atmospheric or higher pressures. The salt precipitates as a fine crystal which can easily be filtered or centrifuged. Sparging is preferably carried out until there is no further uptake of $CO_2$, which can be determined by monitoring the increasing weight of the solution; when the weight becomes constant, sparging is stopped. Since the amine salt can be decomposed by heating, when TMEDA is decomposed in higher boiling hydrocarbons (such as nonane) in which the diamine is moderately soluble, it can be recovered in a very pure crystalline form. Suitable hydrocarbons are those in which the amine is soluble and which have a high enough boiling point to allow the decomposition of the salt. If the amine salt is decomposed in water, TMEDA remains in aqueous solution or is preferably recovered as the diacetate salt (such as by addition of glacial acetic acid) or as the salt of an inorganic acid by stripping the water.

EXAMPLE 1

Chromium-modified Raney cobalt (3.6 g) was washed with deaerated, deionized water, followed by a wash with deaerated MEK, and then added to a one liter autoclave, previously flushed with nitrogen, containing 100 mls. of MEK. The autoclave was purged with hydrogen, heated to 80° C., and then pressurized to 100 psig with hydrogen.

A solution of 2,3-dimethyl-3,3-dinitrobutane in MEK (275 ml, 11 wt % DMDNB) was fed to the autoclave by a metering pump at a rate of 1.5 mls per minute (which was equivalent to a SV of 2.3) over the course of three hours. At the completion of the reaction, the contents of the autoclave were removed and filtered. Analysis of the filtrate (325.9 g) showed the yield of TMEDA to be 82.5%.

EXAMPLE 2

Following the procedure of Example 1, chromium-promoted Raney cobalt catalyst (3.6 g) and 100 ml MEK were added to the oxygen-free autoclave which was then heated to 80° C. and pressurized to 100 psig with hydrogen.

A solution of DMDNB in MEK (170 mls, 11 wt % DMDNB) was fed to the reactor at a rate of 1.5 mls per minute (SV=2.3) over a period of two hours. The autoclave was then cooled, agitation was stopped, and 131.3 g of solution was discharged from the autoclave through a dip tube.

The reactor was reheated to 80° C., hydrogen pressure was adjusted to 100 psig, and 330 mls of DMDNB solution was fed to the reactor at a rate of 1.5 mls over a period of 3.75 hours. The reactor was cooled and the contents of the reactor were removed and filtered. The weight of the filtrate was 334.6 g. Analysis of the combined solutions (465.9 g) showed the yields of TMEDA to be 95.0%.

EXAMPLE 3

Carbon dioxide was sparged through a stirred solution of MEK (480.4 g) from the hydrogenator containing crude TMEDA (0.209 mole). A white crystalline precipitate was formed. Sparging was continued until there was no further uptake of $CO_2$. This was determined by monitoring the increasing weight of the solution; when the weight became constant, sparging was stopped. The weight of the filtered crystals was 34.9 g (0.218 mole). $CO_2$ analysis of the salt showed a 1:1 mole ratio of $CO_2$ to TMEDA. This was essentially a quantitative recovery.

EXAMPLE 4

TMEDA amine salt (138.2 g, containing 100 g TMEDA) was added to a nonane solution (254.3 g) containing 87 g TMEDA. The total available TMEDA in solution was 187.0 g. The solution was heated at 129° C. until $CO_2$ evolution ceased. The solution was then cooled to 2° C. to crystallize TMEDA. After filtration, the weight of TMEDA recovered was 175.5 g, or 94.0% of available amine.

A second addition of amine salt (113.4 g) was added to the filtrate (180.0 g), which still contained 35.1 g TMEDA. The solution was cooled to 5° C. to crystallize TMEDA. The weight of TMEDA recovered was 100.1 g or 85% of the amine in solution.

EXAMPLE 5

TMEDA amine salt (690.0 g) was added to 65° C. water (500 g) and the temperature slowly raised to the boiling point. A nitrogen sparge was used to remove $CO_2$ from solution to prevent its recombination with the amine. When all of the $CO_2$ had been removed, the concentration of free base in water was 39.9%, a recovery of 77.8%. (There was some loss of material due to entrainment by the gas stream.)

What is claimed is:

1. A process for the preparation of tetramethylethylenediamine, comprising reducing 2,3-dimethyl-2,3-dinitrobutane with hydrogen in the presence of a chromium promoted Raney cobalt catalyst, said reduction being carried out by reacting said 2,3-dimethyl-2,3-dinitrobutane with said hydrogen while avoiding accumulation of 2,3-dimethyl-2,3-dinitrobutane in the reaction medium.

2. The process of claim 1, wherein the accumulation of 2,3-dimethyl-2,3-dinitrobutane is avoided by reacting it at a rate no greater than its rate of reaction with hydrogen.

3. The process of claim 1, further comprising recovering tetramethylethylenediamine by sparging with carbon dioxide to form tetramethylethylenediamine salt, and heating the resulting solution to evolve carbon dioxide and to recover the tetramethylethylenediamine.

4. The process of claim 1, wherein the reaction is conducted using a space velocity of from 0.1 to 10.

5. The process of claim 1, wherein the reaction is conducted using a space velocity of from 2 to 5.

6. The process of claim 3, wherein the reaction is conducted using a space velocity of from 0.1 to 10.

7. The process of claim 3, wherein the reaction is conducted using a space velocity of from 2 to 5.

8. The process of claim 1, wherein said 2,3-dimethyl-2,3-dinitrobutane is dissolved in an inert solvent selected from methyl ethyl ketone, methanol, ethanol and N,N-dimethylacetamide.

9. The process of claim 3, wherein said 2,3-dimethyl-2,3-dinitrobutane is dissolved in an inert solvent selected from methyl ethyl ketone, methanol, ethanol and N,N-dimethylacetamide.

10. The process of claim 1, wherein said reduction is conducted in an oxygen-free atmosphere.

11. The process of claim 2, wherein said reduction is conducted in an oxygen-free atmosphere.

12. The process of claim 1, wherein said 2,3-dimethyl-2,3-dinitrobutane is added to a reaction vessel continuously at a rate equal to or slower than it's reaction rate with hydrogen, and wherein reaction product is removed from said vessel at said rate.

* * * * *